United States Patent
Foland et al.

(10) Patent No.: US 7,903,781 B2
(45) Date of Patent: Mar. 8, 2011

(54) DETERMINATION OF HEAVY PARTICLE STOPPING POWER

(75) Inventors: Andrew Dean Foland, Cambridge, MA (US); Boris Oreper, Newton, MA (US)

(73) Assignee: L-3 Communications Security and Detection Systems, Inc., Woburn, MA (US)

(*) Notice: Subject to any disclaimer, the term of this patent is extended or adjusted under 35 U.S.C. 154(b) by 20 days.

(21) Appl. No.: 12/434,440

(22) Filed: May 1, 2009

(65) Prior Publication Data

US 2009/0274269 A1    Nov. 5, 2009

Related U.S. Application Data

(60) Provisional application No. 61/049,836, filed on May 2, 2008.

(51) Int. Cl.
*G01F 1/66* (2006.01)

(52) U.S. Cl. .............................. 378/51; 378/65

(58) Field of Classification Search .............. 378/65, 378/205, 51, 54; 250/492.3, 505.1, 396 R
See application file for complete search history.

(56) References Cited

U.S. PATENT DOCUMENTS

| | | | |
|---|---|---|---|
| 4,365,341 A * | 12/1982 | Lam | 378/65 |
| 4,792,900 A | 12/1988 | Sones et al. | |
| 5,319,547 A | 6/1994 | Krug et al. | |
| 5,600,700 A | 2/1997 | Krug et al. | |
| 5,642,393 A | 6/1997 | Krug et al. | |
| 5,838,758 A | 11/1998 | Krug et al. | |
| 6,088,423 A | 7/2000 | Krug et al. | |
| 6,316,773 B1 | 11/2001 | Giakos | |
| 7,577,236 B2 * | 8/2009 | Nose et al. | 378/119 |
| 2006/0122500 A1 | 6/2006 | Heismann et al. | |
| 2007/0133733 A1 | 6/2007 | Popa-Simil | |
| 2007/0225603 A1 | 9/2007 | Jackson | |
| 2008/0082002 A1 | 4/2008 | Wilson et al. | |
| 2009/0129545 A1 * | 5/2009 | Adler et al. | 378/65 |
| 2009/0154645 A1 * | 6/2009 | Lifshitz et al. | 378/65 |

OTHER PUBLICATIONS

International Search Report and Written Opinion for corresponding International Application No. PCT/US09/042692, mailed Jul. 1, 2009, 10 pages.

Lehmann, L.A., et al., "Generalized Image Combinations in Dual KVP Digital Radiography," *Med. Phys.*, vol. 8, No. 5, Sep./Oct. 1981, pp. 659-667.

*Aspects of Explosives Detection*, Marshall, M. and Oxley, J.C., eds., Sections 2.3-2.5, Elsevier, 2009.

Tsunoo, T., et al., "Distribution of Electron Density Using Dual-Energy X-Ray CT," *IEEE Transactions on Nuclear Science*, vol. 50, No. 5, Oct. 2003, pp. 1678-1682.

* cited by examiner

*Primary Examiner* — Hoon Song
(74) *Attorney, Agent, or Firm* — Fish & Richardson P.C.

(57) ABSTRACT

A distribution of heavy particle stopping power is be determined. A distribution of effective atomic number of a three-dimensional space is accessed, and a distribution of an x-ray stopping power of the three-dimensional space is accessed. A conversion is applied to the distribution of the effective atomic number and the distribution of x-ray stopping power. A distribution of the heavy particle stopping power of the three-dimensional space is generated based on the conversion, the heavy particle stopping power being an indication of a depth of penetration for a heavy particle incident on the three-dimensional space.

28 Claims, 3 Drawing Sheets

DETERMINATION OF HEAVY PARTICLE STOPPING POWER

CROSS-REFERENCE TO RELATED APPLICATION

This application claims the benefit of U.S. Provisional Application No. 61/049,836, filed May 2, 2008 and titled MULTI-ENERGY X-RAY IMAGING, which is incorporated by reference in its entirety.

TECHNICAL FIELD

This description relates to determination of heavy particle stopping power.

BACKGROUND

Heavy particle therapy (such as proton therapy or heavy ion therapy) and/or hadron therapy (e.g., treatments that deliver pions) may be used to treat tumors within a human patient. In general, heavy particle therapy involves aiming energetic ionizing particles accelerated by a particle accelerator toward a target tumor. Because of their relatively large mass, the heavy particles have a relatively localized deposition of energy within the tissue. Thus, as compared to other radiation treatments, heavy particle therapy may be less likely to cause damage to surrounding tissue.

SUMMARY

A three-dimensional space (such as a portion of a patient's body) is exposed to dual-energy x-ray radiation, and radiation passing through the three-dimensional space is sensed and used to determine a distribution of effective atomic number and a distribution of an x-ray stopping power of the three-dimensional space. A conversion is applied to the distribution of effective atomic number and the distribution of the x-ray stopping power to generate a distribution of the heavy particle stopping power. The distribution of the heavy particle stopping power may be used to more accurately plan a treatment with heavy particles (such as a proton therapy treatment that treats a tumor with protons) as compared to techniques that rely on the distribution of the x-ray stopping power. In some implementations, a source of the dual-energy x-ray radiation may be co-located with a heavy particle treatment system. In these implementations, the dual-energy x-ray source may be used to image a portion of a patient while, or shortly before, the heavy particle treatment system applies heavy particle treatment to the imaged portion of the patient.

In one general aspect, a system for determining a distribution of heavy particle stopping power of a patient includes a broadband source of dual-energy x-rays. The broadband source is configured to produce a beam of broadband x-ray radiation, the broadband beam including energy having a first energy spectrum and a first peak energy and energy having a second energy spectrum and a second peak energy, and irradiate a three-dimensional space within a patient with the beam of broadband x-ray radiation. The system also includes a detector system. The detector system includes a sensor configured to sense radiation from the three-dimensional space, the sensed radiation including radiation caused by irradiating the three-dimensional space with the broadband source, and to produce a representation of the sensed radiation.

The system also includes a processor operable to receive the representation of the sensed radiation, determine a distribution of effective atomic number of the three-dimensional space based on the representation from the detector system, determine a distribution of an x-ray stopping power of the three-dimensional space based on the representation from the detector system, the x-ray stopping power of the three-dimensional space being an indication of a depth of penetration of an x-ray incident on the three-dimensional space, apply a conversion to the distribution of the x-ray stopping power and the distribution of the effective atomic number, and generate a distribution of a heavy particle stopping power of the three-dimensional space based on the conversion, the heavy particle stopping power being used to indicate a depth of penetration for a heavy particle incident on the three-dimensional space.

Implementations may include one or more of the following features. The processor may be further operable to produce an input sufficient to define a heavy particle treatment based on the heavy particle stopping power, and the input may include including a depth of penetration for a particular heavy particle. The system also may include a heavy particle therapy system. The heavy particle therapy system may include a source of heavy particles configured to produce a beam including a heavy particle, and direct the beam to a position within the three-dimensional space. The heavy particle therapy system also may include an input module configured to receive the distribution of the heavy particle stopping power of the three-dimensional space from the processor.

The heavy particle therapy system and the broadband source of dual-energy x-rays may be co-located. The heavy particle therapy system and the broadband source of dual-energy x-rays may be located on a gantry. The system may include a gantry on which the broadband source of dual-energy x-rays and the detector system are mounted. The broadband source of dual-energy x-rays may include a single broadband source that is switchable between a first mode and a second mode, the single broadband source producing a first x-ray beam in the first mode and a second x-ray beam in the second mode, the first x-ray beam having the first energy spectrum and the first peak energy, and the second x-ray beam having the second energy spectrum and the second peak energy.

In some implementations, the broadband source of dual-energy x-rays includes a first broadband source configured to produce a first x-ray beam having the first energy spectrum and the first peak energy, and a second broadband source separate from the first broadband source and configured to produce a second x-ray beam having the second energy spectrum and the second peak energy. The detector system may be positioned opposite the three-dimensional space relative to the broadband source.

In another general aspect, a system for determining a distribution of heavy particle stopping power of a patient includes a broadband source of x-rays configured to produce a single beam of broadband x-ray radiation having an energy spectrum and a peak energy, and irradiate a three-dimensional space within a patient with the beam of broadband x-ray radiation. The system also includes a dual-energy detector system comprising a first sensor including a first sensor relatively more sensitive to a first band of energies included in the broadband x-ray radiation, and a second sensor relatively more sensitive to a second band of energies included in the broadband x-ray radiation, the second band of energies being higher than the first band of energies. The sensor is configured to sense radiation from the three-dimensional space, the sensed radiation including radiation caused by irradiating the three-dimensional space with the broadband source, and produce a representation of the sensed radiation.

The system also includes a processor operable to receive the representation of the sensed radiation, determine a distribution of effective atomic number of the three-dimensional space based on the representation from the detector system, determine a distribution of an x-ray stopping power of the three-dimensional space based on the representation from the detector system, the x-ray stopping power of the three-dimensional space being an indication of a depth of penetration of an x-ray incident on the three-dimensional space, apply a conversion to the distribution of the x-ray stopping power and the distribution of the effective atomic number, and generate a distribution of a heavy particle stopping power of the three-dimensional space based on the conversion, the heavy particle stopping power being used to indicate a depth of penetration for a heavy particle incident on the three-dimensional space.

In another general aspect, a computer-readable storage medium stores instructions, that when executed, cause a processor to access data reflecting an interaction between a broadband x-ray beam and a three-dimensional space of a patient, the broadband x-ray beam including a first energy band having a first energy spectrum and a first peak energy, and a second energy band having a second energy spectrum and a second peak energy higher than the first peak energy. The accessed data is analyzed to determine an interaction between the three-dimensional space and the first energy band and an interaction between the three-dimensional space and the second energy band, and a distribution of effective atomic number of a three-dimensional space is determined based on the interactions between the three-dimensional space and the first and second energy bands. A distribution of x-ray stopping power of the three-dimensional space is accessed, and a conversion is applied to the distribution of the effective atomic number and the distribution of the x-ray stopping power of the three-dimensional space. A heavy particle distribution that represents a heavy particle stopping power of the three-dimensional space is generated based on the conversion. The heavy particle stopping power is used to indicate a depth of penetration for a heavy particle incident on the three-dimensional space.

Implementations may include one or more of the following features. Inputs sufficient to define a heavy particle treatment that is directed toward a particular space within the three-dimensional space may be provided. The inputs may be derived from the heavy particle distribution and the inputs including a depth of penetration for a particular heavy particle. The inputs may include a three-dimensional location of a target space within a body of a patient. The particular heavy particle may be one of a proton, a heavy ion, or a pion. The first energy spectrum and the second energy spectrum may overlap. The three-dimensional space may be represented by one or more voxels, and the distribution of the effective atomic number includes an effective atomic number for each voxel. The heavy particle distribution may be a volumetric heavy particle stopping power distribution. The heavy particle distribution may be a two-dimensional stopping power distribution.

In another general aspect, a distribution of heavy particle stopping power is determined. A distribution of effective atomic number of a three-dimensional space is accessed, and a distribution of an x-ray stopping power of the three-dimensional space is accessed. A conversion is applied to the distribution of the effective atomic number and the distribution of x-ray stopping power. A distribution of the heavy particle stopping power of the three-dimensional space is generated based on the conversion, the heavy particle stopping power being an indication of a depth of penetration for a heavy particle incident on the three-dimensional space.

Implementations may include one or more of the following features. The distribution of the heavy particle stopping power distribution may be a volumetric distribution. The distribution of the heavy particle stopping power distribution may be a two-dimensional distribution.

Implementations of any of the techniques described above may include a method, a process, a system, a device, an apparatus, or instructions stored on a computer-readable storage medium. The details of one or more implementations are set forth in the accompanying drawings and the description below. Other features will be apparent from the description and drawings, and from the claims.

DETAILED DESCRIPTION

Figure 1:
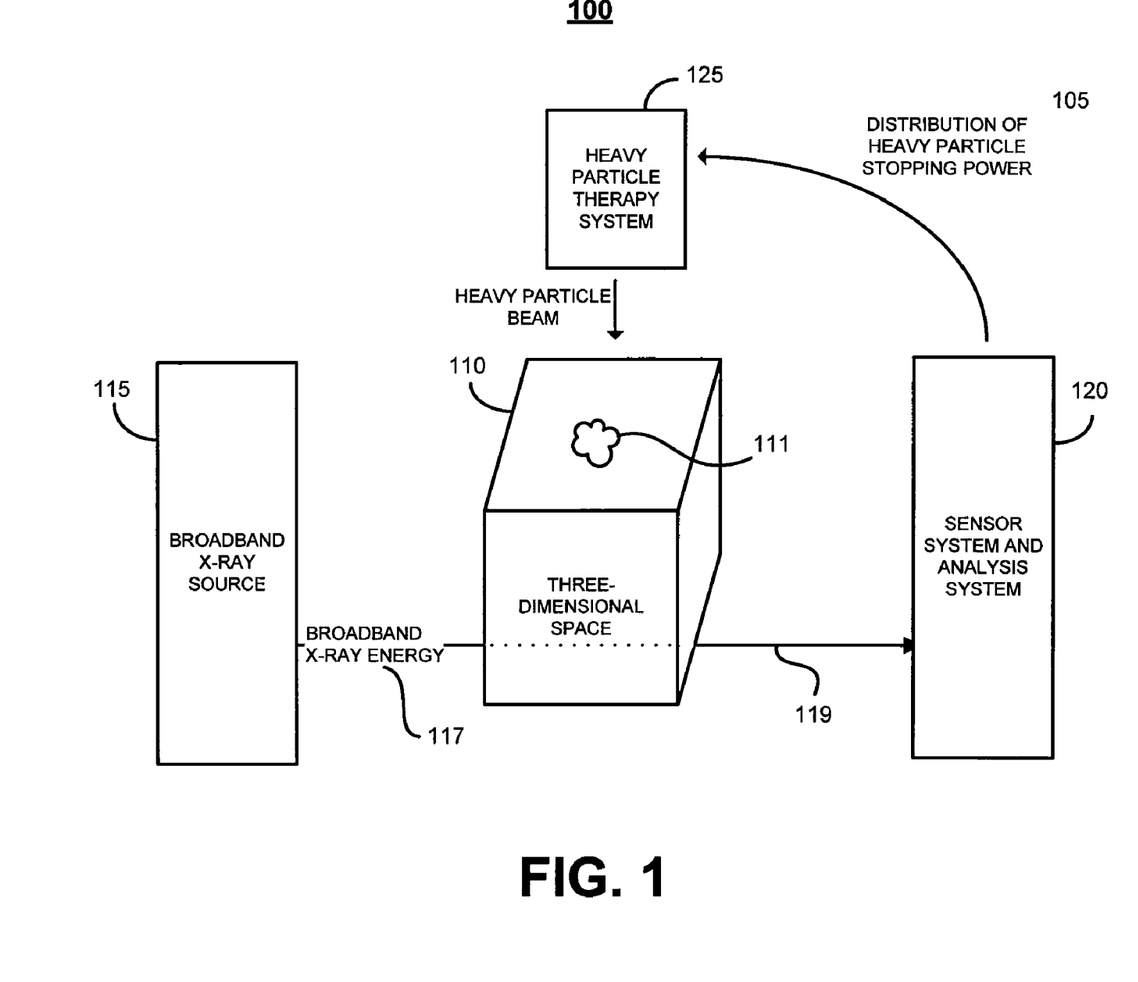
FIG. 1 is an illustration of an example system that determines a distribution of heavy particle stopping power of a three-dimensional space.

Referring to FIG. 1, an illustration of an example system 100 that determines a distribution of heavy particle stopping power 105 of a three-dimensional space 110 is shown. The three-dimensional space 110 may be a portion of a body of a human patient that is being treated with heavy particle therapy (such as proton therapy) to remove a cancerous tumor 111, and the three-dimensional space 110 also may be considered to be a region or a volume. The distribution 105 is a distribution or representation of a heavy particle stopping power of the space 110, and the distribution 105 provides an indication of a depth of penetration of a heavy particle that is incident on the three-dimensional space 110. The distribution 105 also may be referred to as a mapping or a distributional mapping. In particular, the distribution 105 may provide a distribution of the heavy particle stopping power that occurs throughout the patient. The distribution 105 may be used to plan heavy particle therapy, such as a medical treatment that uses a beam of heavy particles to irradiate and destroy a tumor located within the space 110.

Techniques are described below for using multi-energy X-ray imagery (such as imagery from a dual-energy x-ray system) in medical applications. For example, the techniques described below may be used to plan for heavy particle therapy (such as proton therapy or heavy ion therapy) and/or to plan hadron therapy (e.g., treatments that deliver pions to a tumor). In one example, proton therapy may be used to treat cancer patients by directing protons toward a cancerous tumor that is in a localized region within the patient. In general, heavy particle therapy involves aiming energetic ionizing particles accelerated by a particle accelerator toward a target tumor. Because of their relatively large mass, the heavy particles undergo minimal scattering within the tissue, thus, as compared to other radiation treatments, heavy particle therapy may be less likely to cause damage to surrounding tissue. Additionally, the heavy particles have a particular depth range (expressed as the stopping power of the region to be treated) and are unlikely to travel more deeply into the tissue than the expected depth. The dose delivered to the tissue is maximum in the last few millimeters of the particle's range, and this maximum may be referred to as the Bragg peak. Thus, because the heavy particles travel to relatively localized region within a space, the heavy particle treatment may result in minimal collateral damage if the stopping power of the region is known.

The techniques discussed below result in a real-time, substantially real-time or near-real-time reconstruction of the heavy particle-stopping-power distribution occurring inside a patient who is undergoing proton therapy. The heavy particle stopping power distribution may be a volumetric image that indicates the heavy particle stopping power of a region of the patient's body that is undergoing proton therapy. These techniques may increase, perhaps, significantly increase, the viability of proton therapy, other types of heavy particle therapy, and/or hadron therapy.

Some approaches to heavy particle therapy may face significant challenges because imaging systems measure either x-ray stopping power (in the case of a conventional x-ray computed tomography (CT)) or magnetic susceptibility (in the case of magnetic resonance imaging (MRI)). Neither of these measures correlate perfectly with heavy particle stopping power, which is a relevant clinical therapeutic quantity because the heavy particle stopping power provides an indication of how deeply the heavy particles travel into the region. Thus, the heavy particle stopping power may allow heavy particles to be more directly and accurately delivered to the tumor. For example, x-ray stopping power, which represents the depth of penetration by an x-ray incident on the region of the patient undergoing treatment, shows how deeply an x-ray travels into the patient. However, the x-ray stopping power generally does not show how deeply a heavy particle (such as a proton, a heavy ion, or a pion) travels into the patient. Thus, using the x-ray stopping power to plan a treatment that applies heavy particles to a patient may result in the heavy particles reaching tissue surrounding a targeted tumor instead of, or in addition to, reaching the targeted tumor. Thus, the treatment may be unsuccessful or only partially successful because the tissue surrounding the tumor may be damaged. Additionally, the heavy particles may miss the tumor, resulting in the tumor remaining in the patient even after the treatment.

This challenge generally may limit the usefulness of heavy particle therapy. One approach for dealing with the measurement challenge is to try to correct MRI or conventional x-ray computed tomography (CT) images. This approach may result in substantial loss in spatial resolution. As discussed below, a distribution of effective atomic number of the space to be treated may be derived by exposing the space to dual-energy x-ray radiation, and the distribution of the heavy particle stopping power of the space may be generated based on the distribution of the effective atomic number.

The described techniques reconstruct the patient heavy particle-stopping-power distribution from multi-energy x-rays. The techniques may use multi-energy or spectral techniques, including dual-energy x-rays. In some implementations, the multi-energy x-rays may be obtained in real time, substantially in real time, or in near real-time. In some implementations, the multi-energy x-rays may be generated by a dual-energy CT system. The techniques may be applied, for example, in a medical system that is co-located with a proton therapy machine or other type of heavy particle therapy machine in a hospital setting.

In greater detail, the system 100 generates a distribution 105 of the heavy particle stopping power of the space 110. The distribution 105 may be a volumetric image of the space 110 that is made up of voxels, each of which represents a physical volume within the space 110. Each voxel in the distribution 105 represents a heavy particle stopping power of the physical volume represented by the voxel. The distribution of the effective atomic number and the x-ray stopping power may be converted to the distribution of the heavy particle stopping power. In some implementations, the distribution 105 may be a two-dimensional slice of a volumetric image.

The system 100 includes a broadband source 115 that exposes the space 110 to broadband x-ray energy 117. The space 110 may be a three-dimensional space that is part of a human patient's body. The broadband x-ray radiation 117 enters the space 110, travels through the space 110, and is attenuated by an amount that depends on the composition of the space 110. For example, if the space 110 includes dense material such as bone, the broadband x-ray radiation 117 is attenuated more than the radiation 117 would be attenuated by passing through lower density material such as soft tissue.

Attenuated radiation 119 is sensed by a sensor and analysis system 120, which determines, from the attenuated radiation 119, a distribution of the effective atomic number for the space 110 and a distribution of the x-ray stopping power of the space 110. As discussed in greater detail below with respect to FIG. 3, the distribution of the effective atomic number of the space 110 and the distribution of the x-ray stopping power of the space 110 is converted into the distribution 105 of the heavy particle stopping power of the space 110. The distribution 105 and/or inputs derived from the distribution 105 may be provided to a heavy particle therapy system 125. The heavy particle therapy system 125 delivers heavy particles to the space 110 in order to treat the space 110 or a portion of the space 110, such as the tumor 111.

Figure 2:
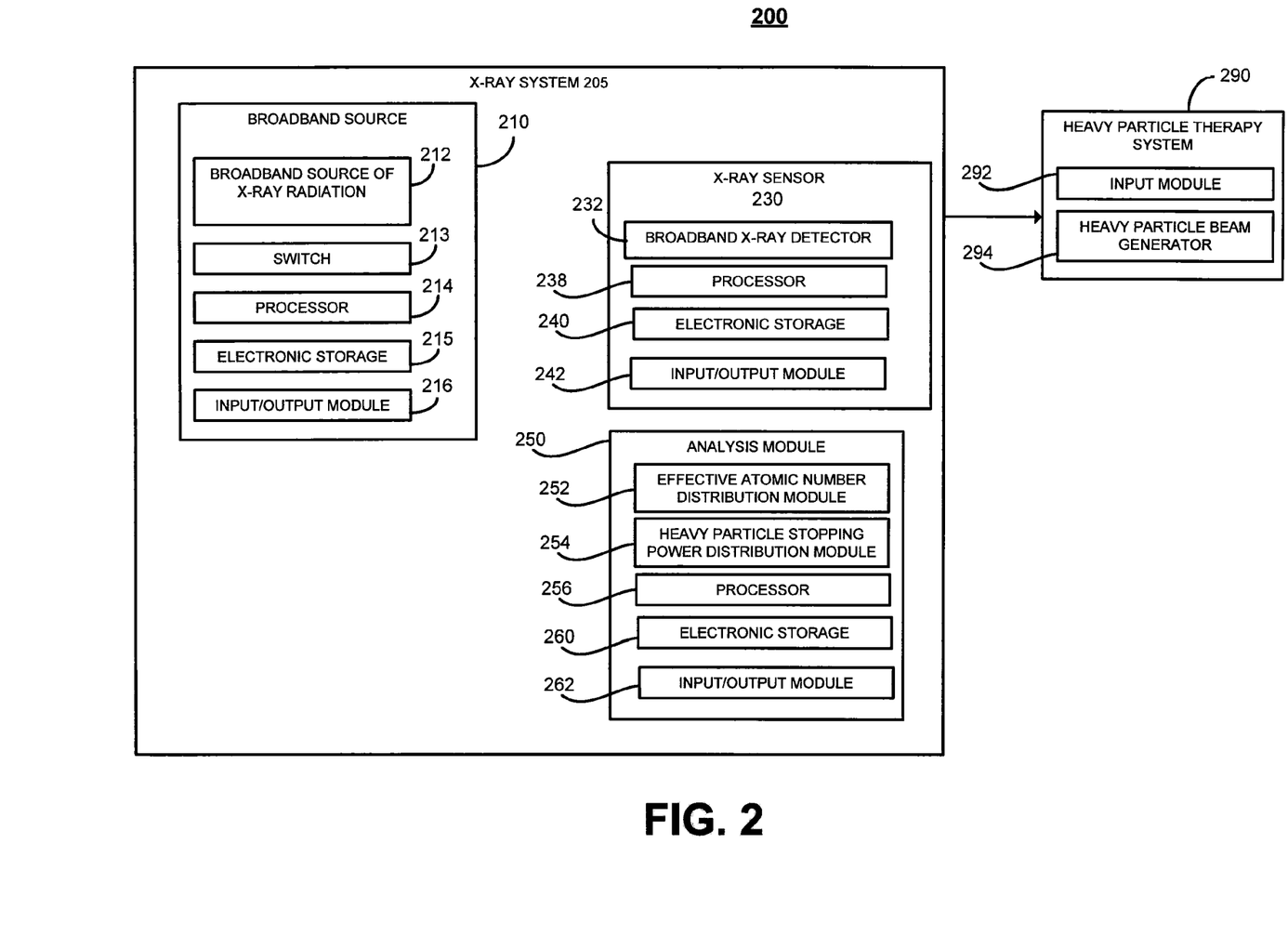
FIG. 2 is a block diagram of an example system that determines a distribution of heavy particle stopping power and provides inputs based on the distribution to a heavy particle therapy system.

Referring to FIG. 2, a block diagram of an example system 200 is shown. The system 200 is a system that determines a distribution of a heavy particle stopping power of an imaged space or region. The distribution of the heavy particle stopping power may be used to provide inputs to a heavy particle therapy system 290. The system 200 may be similar to the system 100 discussed above with respect to FIG. 1.

The system 200 includes an x-ray system 205 that is co-located with the heavy particle therapy system 290. The x-ray system 205 includes a broadband source 210, an x-ray sensor 230, and an analysis module 250. The broadband source 210 produces broadband x-ray radiation, and the broadband source 210 includes a broadband source of x-ray radiation 212, a processor 214, and electronic storage 215, and an input/output module 216. The broadband source 210 may be, for example, a dual-energy CT scanner.

The broadband source of x-ray radiation 212 may produce a single broadband x-ray beam having an energy spectrum and a maximum energy. The maximum energy may be, for example, between 180 KeV and 200 KeV. The broadband source of y x-ray radiation 212 may be, for example, one or more x-ray generators. In some implementations, the broadband source of radiation 212 includes two sources, each of which produce a single broadband x-ray beam. In another example, the broadband source of x-ray radiation 212 may be switchable between two modes by way of a switch 213. In this example, the broadband source of x-ray radiation 212 produces an x-ray beam having a first band of energies or a first energy level, and during the other mode, the broadband source 212 produces an x-ray beam having a second band of energies that include higher energies than those included in the first energy band. The first band of energies may be referred to as the low energies and the second band may be referred to as the high energies.

An energy band may be defined by an energy spectrum and a peak energy (e.g., a maximum energy). Thus, the broadband x-ray radiation produced by the source 212 includes x-ray radiation having a first energy spectrum and a first peak energy, and x-ray radiation having a second energy spectrum and a second peak energy. Thus, although in some implementations, the broadband source 210 produces one x-ray beam and exposes a three-dimensional space to the single x-ray beam, the space is exposed to x-rays of two different energy spectrums or bands. Additionally, the broadband source 210 may produce a single broadband x-ray beam having a single energy spectrum and a maximum energy. In these implementations, two detectors may be used to detect different portions of the single energy spectrum. Thus, as explained with respect to FIG. 3, information about the region (such as the effective atomic number of the region) may be extracted from radiation attenuated by the imaged region.

The broadband source 210 also includes a processor 214, an electronic storage 215, and an input/output module 216. The electronic storage 215 stores instructions, perhaps as a computer program, that, when executed, cause the processor to communicate with other components in the broadband source 210. For example, the electronic storage 215 may store control commands that are transferred to the switch 213 determine the timing of switching the broadband source between producing x-ray radiation having different energy spectra.

The input/output module 216 provides an interface that allows data and/or commands to be input to the sensor 230 and/or read from the sensor 230. The input/output module 216 may receive data from a tactile device such as a keyboard, a mouse, a communications port, or a display. The input/output module 216 also may include software that allows communication between the sensor 230, the components of the sensor 230, and/or an external device.

The dual-energy system 205 also includes the x-ray sensor 230. The sensor 230 includes a broadband x-ray detector 232. The broadband x-ray detector 232 senses radiation from the imaged region. The sensed radiation is radiation that originated from the broadband source 210, passed through the imaged region and was attenuated by the materials in the region, and emerged from the region to be detected by the broadband x-ray detector 232. Thus, the x-ray radiation sensed by the broadband x-ray detector 232 may be used to determine how much attenuation of the initial x-ray beam occurs due to the beam passing through the imaged region.

The ratio of the amount of attenuation of a relatively high-energy x-ray beam (e.g. a beam having a maximum energy of 180 KeV to 200 KeV) to the amount of attenuation of a relatively low-energy x-ray beam (e.g., a beam having a maximum energy of about 100 KeV) may be used to determine the effective atomic number of the material through which the high-energy and low-energy beams pass. Because the beam from the broadband source 210 is not monochromatic, even in implementations in which the broadband source 210 produces a single broadband beam, but is instead a spectrum composed of many different x-ray energies, the beam from the broadband source 210 includes at least two energies. The use of two detectors allows one to differentiate attenuations on the relatively low end of the spectrum, as compared to the relatively high end of the spectrum. The relatively low end of the spectrum and the relatively high end of the spectrum are not necessarily strictly two different spectra with a sharp dividing point—the two detectors have different sensitivities with different weights over the whole spectrum of the broadband beam. Use of the two detectors allows decomposition of the single broadband beam as if the beam were two beams of relatively lower and relatively higher energies. So in turn, that allows one to decompose the attenuation into a density and an effective atomic number (Z-effective).

In some implementations, the broadband x-ray detector 232 may be a solid-state detector (such as a Ge (Germanium) detector or a CZT (Cadmium Zinc Telluride) detector) that produces electrons (e.g., an electrical current) in response to being struck by x-ray radiation. The amount of electrons produced by the solid-state-detector is proportional to the energy of the photons in the x-ray radiation that strikes the detector. Additionally, the solid-state detector produces a count of the number of photons per energy bin (e.g., a particular energy or range of energies), and the count for each bin may be read out from the solid-state detector through a channel for each bin.

For example, the broadband source may produce x-ray radiation having a maximum energy of 200 KeV, and the x-ray detector 232 may have five read-out channels, each of which produce an electrical signal proportional to the number of photons in a range of energies that strike the detector. For example, the first channel may correspond to photons below 80 KeV, the second channel between 80 KeV and 110 KeV, the third channel between 110 KeV and 140 KeV, the fourth channel between 140 KeV and 170 KeV, and the fifth channel between 170 KeV and 200 KeV. The electrons from each channel may be measured to produce a histogram of the number of electrons produced by the detector per energy bin. This histogram is proportional to the number of photons that strike the detector having energy within the range of the bins. Photons associated with bins of energies that are lower than a particular energy (e.g., 100 KeV) may be considered low-energy photons, and photons associated with the higher-energy bins may be considered high-energy photons. Thus, using the solid-state detector, the total amount of "low" energy photons and the amount of total "high" energy photons emitted from a region irradiated with broadband x-ray radiation may be determined. The ratio between the number of high-energy photons and low-energy photons may be used to determine the effective atomic number of the region.

In some implementations, the broadband x-ray detector 232 may be a stack of two scintillating crystals that are positioned one behind the other. The two-crystal stack is aligned with respect to the imaged space such that x-rays emanating from the space strike one of the crystals in the two-crystal stack first. For the purposes of this discussion, the crystal that is struck first is referred to as the front detector, and the other detector is referred to as the back detector. Scintillators produce visible light in response to being struck by x-ray radiation, and the intensity of the visible light is proportional to the intensity of the x-ray radiation that strikes the scintillator. The scintillating crystal may be a material such as cadmium tungstate ($CdWO_4$ or CWO), thallium-activated cesium iodide CsI (Tl), cadmium zinc telluride, and rare-earth phosphors. The front detector and the back detector are individually coupled (e.g., optically coupled or coupled by direct physical connection) to optical detectors that are sensitive to visible light. The visible light detectors produce an electrical signal that is proportional to the amount of sensed visible light. The visible light detector may be, for example, a photomultiplier tube (PMT) or a photodiode. Thus, this implementation includes an optical detector for each scintillator, and the output of the optical detector represents the amount of x-ray radiation incident on the scintillator to which the detector is attached.

Almost all x-ray photons emerging from the imaged space reach the front detector, and relatively low-energy photons are deposited on the front detector rather than penetrating through to the back detector. However, photons with relatively high energy pass through the front detector and reach the back detector. Thus, the visible light produced as a result of the relatively low-energy photons striking the front detector is more strongly weighted to represent the amount of low-energy photons striking the detector 232, and the visible light produced as a result of the relatively high-energy photons striking the detector 232 is more strongly weighted to represent the number of high-energy photons striking the detector 232. Accordingly, by measuring the intensity of the visible light from the detector coupled to the front detector and the detector coupled to the back detector, an amount of low-energy radiation and an amount of high-energy radiation may be respectively inferred. The effective atomic number of the imaged space may be determined from the ratio of the high-energy radiation attenuation to the low-energy radiation attenuation.

Regardless of the type of detector or sensor used in the broadband detector 232, the x-ray sensor 230 may include many broadband detectors (e.g., thousands) such the broadband detector 232, and the detectors may be arranged in an array or line along the imaged region.

The sensor 230 also includes a processor 238, an electronic storage 240, and an input/output module 242. The electronic storage 240 may store representations of the signal produced by the broadband x-ray detector 232 in order to, for example, generate an image of the region from with the radiation is sensed by the sensor 230. The electronic storage 240 also may include instructions, that when executed, cause the processor 238 to retrieve data from the electronic storage 240 and/or store data from the sensor 230 in the electronic storage 240. The sensor 230 also includes the input/output module 242. Data and/or control commands, for example, may be provided to the sensor 230 or from the sensor 230 through the input/output module 242.

The dual-energy x-ray system also includes an analysis module 250 that produces a distribution of heavy particle stopping power using data from the sensor 230. The analysis module 250 includes an effective-atomic number distribution module 252 that determines an effective atomic number for the imaged region using the radiation sensed by the sensor 230. Determination of the effective atomic number is discussed in more detail with respect to FIG. 3. The analysis module 250 also includes a heavy particle stopping power distribution module 254 that determines the heavy particle stopping power for the region using the effective atomic number distribution and the x-ray stopping power. The analysis module 250 also includes a processor 256, an electronic storage 260, and an input/output module 262. The electronic storage 260 may store instructions that, when executed, caused the processor 256 to convert the effective atomic number distribution of the region and the x-ray stopping power distribution of the region into a distribution of the heavy particle stopping power of the region. The analysis module also includes an input/output module 262. The input/output module provides the heavy particle stopping power distribution, and/or inputs derived from the heavy particle stopping power distribution, to the heavy particle therapy system 290. For example, the input/output module 262 receives data to create the x-ray stopping power distribution from the sensor 230, and the input/output module 262 receives data from the broadband x-ray detector 232 used to determine the effective atomic number distribution.

Although the analysis module 250 is shown as part of the dual-energy x-ray system 205, that is not necessarily the case. In some implementations, the analysis module 250 is separate from the dual-energy x-ray system 205 and in communication with the dual-energy x-ray system 205.

The system 200 also includes the heavy particle therapy system 290. The heavy particle therapy system includes an input module 292 and a heavy particle beam generator 294. The heavy particle beam generator may be a particle accelerator that produces a single beam of heavy particles. The input module 292 receives input from the dual-energy x-ray source 205. For example, the input module 292 receives the distribution of the heavy particle stopping power from the dual-energy x-ray system 205 and/or the analysis module 250. In other examples, the input module also may receive, additionally or alternatively, inputs derived from the distribution of the heavy particle stopping power that are sufficient to plan a heavy particle treatment. For example, the inputs may include a depth of penetration of a particular portion of the volumetric distribution that is known to include a tumor to be treated. The inputs may include a location (e.g., three-dimensional coordinates) of a target tumor or other type of target space or region within the patient.

Thus, the heavy particle therapy system 290 is configured to communicate with the dual-energy x-ray system 205. In some implementations, the heavy particle therapy system 290 and the dual-energy x-ray system 205 are co-located together in a hospital setting. In some implementations, the heavy particle therapy system 290 and the dual-energy x-ray system 205 are not co-located, and may provide distribution information (as discussed above) for use by a therapy planning system or other type of planning system. The heavy particle therapy system 290 and the dual-energy x-ray system 205 may be mounted together on a gantry such that a patient in the gantry may be imaged with the dual-energy x-ray system 205 and concurrently, or very soon afterwards, exposed to the heavy particle treatment beam. Such an implementation may allow the heavy particle therapy to be adjusted to account for movement of the patient during imaging, for example.

The electronic storage components 215, 238, and 260 may be volatile memory, such as RAM. In some implementations, and the electronic storage components 215, 238, and 260 may include both non-volatile and volatile portions or components. The processors 214, 238, and 256 may be processors suitable for the execution of a computer program such as a general or special purpose microprocessor, and any one or more processors of any kind of digital computer. Generally, a processor receives instructions and data from a read-only memory or a random access memory or both.

Figure 3:
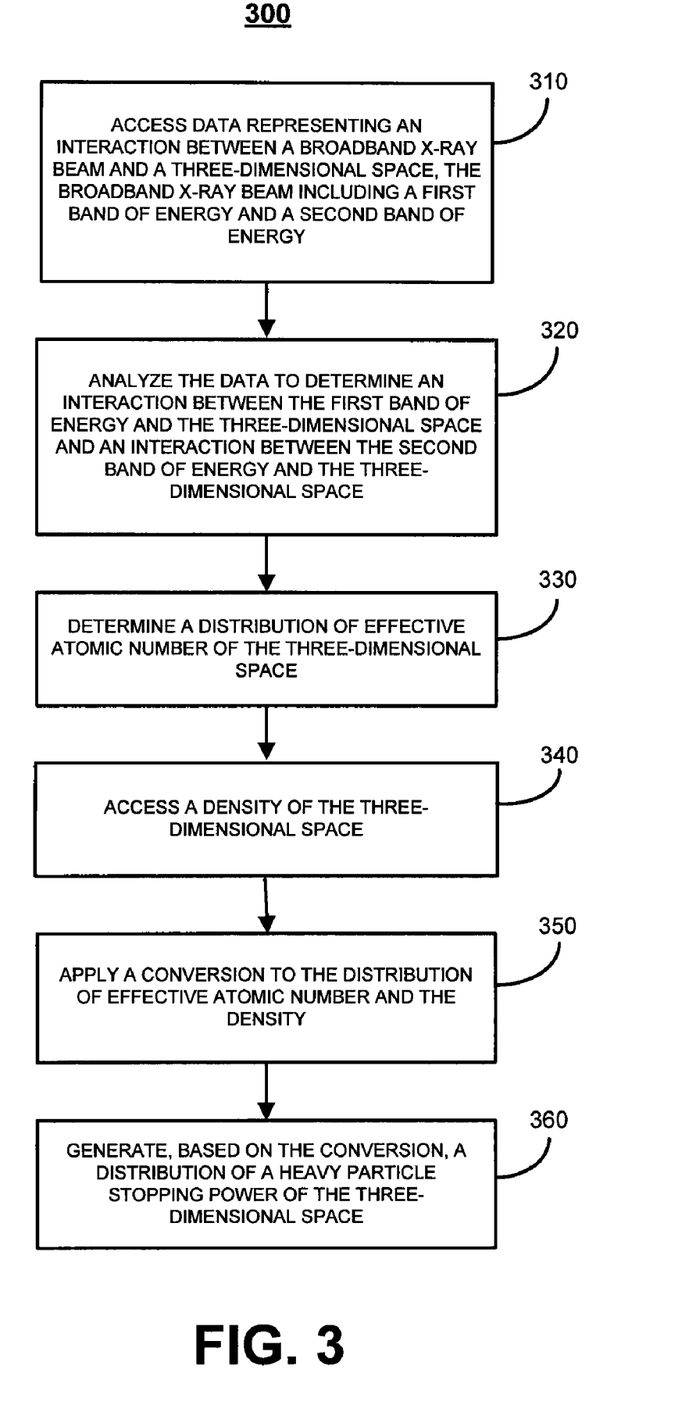
FIG. 3 is an example process for generating a distribution of a heavy particle stopping power of a three-dimensional space.

Referring to FIG. 3, an example process 300 for determining a heavy particle stopping power of a region is shown. The example process 300 may be performed by one or more processors included in a multi-energy x-ray imaging system or one or more processors in communication with a multi-energy x-ray imaging system. The multi-energy x-ray imaging system may be a dual-energy CT system. The process 300 may be performed by the processor 256 that is included in the analysis module 250 discussed above with respect to FIG. 2.

Data representing an interaction between a broadband x-ray beam and a three dimensional space is accessed (310). The broadband x-ray beam may be produced by, for example, the broadband source 210 discussed above with respect to FIG. 2. The broadband x-ray beam includes a first band or spectrum of energy and a second band or spectrum of energy that includes energies that are higher than at least some of the energies in the first band of energy. The first and second bands of energies both have an energy spectrum (e.g., photons having a range of x-ray energies) and a peak (e.g., maximum) energy. For example, the first band of energy may have a maximum energy of 100 KeV and the second band of energy may have a maximum energy of 180 KeV. In other examples, the second band of energy may have a maximum energy between 150 KeV and 200 KeV.

The accessed data is analyzed to determine an interaction between the first band of energy and the three-dimensional space and the second band of energy and the three-dimensional space (320). For example, in some implementations, the broadband source produces an x-ray beam that includes both the first energy band and the second energy band, and the data may be collected with two sensors to distinguish the interactions between the region and the different energy bands. In this example, one of the detectors is sensitive to the first band of energy (e.g., with a peak energy of 100 KeV to continue the above example) and the other is sensitive to the second band of energy (e.g., with a peak energy of 180 KeV in the above example).

The data is analyzed to determine which detector sensed the data. In other implementations, the region may be exposed to the first band of energy and separately exposed to the second band of energy. For example, two separate sources of x-ray energy may be sensed at different times by a single broadband detector that is sensitive to both the first band of energy and the second band of energy. Regardless of how the region is exposed to the first and second bands of energy, the interactions between the region and the first band of energy and the region and the second band of energy are separated from each other such that the interactions may be separately analyzed to determine an effective atomic number distribution of the region. The effective atomic number distribution of the region may be a volumetric image having voxels that each represents a physical volume in an imaged space. Each voxel has a value that represents an effective atomic number of the physical volume represented by the voxel.

A distribution of the effective atomic number of the three-dimensional space is determined (330). The distribution of the effective atomic number of the three-dimensional space is a representation of the effective atomic number throughout the three-dimensional space. The effective atomic number distribution may be a volumetric image made of voxels, with each voxel representing a physical volume within the three-dimensional space. In this example, the value of the voxel represents an effective atomic number of the physical volume that the voxel represents. Thus, the three-dimensional effective atomic number distribution represents the atomic number of the various portions of the three-dimensional space.

As discussed above with respect to (320), the three-dimensional space is exposed to broadband x-ray radiation that has at least two energy bands. In some implementations, the broadband x-ray radiation is a single beam that includes an energy spectrum having at least two energies. In other implementations, the broadband x-ray radiation is two broadband x-ray beams, each having an energy spectrum and a maximum energy, with one having a higher maximum energy than the other. Using information from the interaction between the imaged space and the two energy bands, the effective atomic number throughout the three-dimensional space may be determined. In particular, the effective atomic number of the material within the three-dimensional space may be determined by exposing the material to x-rays of two of more different energies and analyzing the absorption of the x-rays by the materials at the different energies. The effective atomic number is a material-specific property, and the effective atomic number may be referred to as the true Z number. Briefly, materials that readily absorb x-rays, such as metals, tend to have relatively high effective atomic numbers (e.g., above 20). These materials absorb both lower-energy x-rays and higher-energy x-rays. Materials that absorb x-rays less readily, such as organic materials and plastics, tend to have lower effective atomic numbers (e.g., between 5 and 12). These materials tend to absorb fewer low energy x-rays as compared to materials having a higher effective atomic number. Organic materials may include items such as food and clothing, and inorganic materials may include items made from materials such as metal In particular, characteristic differences in photoelectric effect scattering and Compton scattering, and comparison of the pairwise differential attenuation of the higher energy x-rays and the lower energy x-rays may be used to determine whether differences in attenuation may be attributed to the presence of a specific material having a particular effective atomic number. The presence of the specific material may be determined regardless of whether the material is overlayed (e.g., covered) or underlayed (e.g., covering) by a different material of a different atomic number. Techniques for determining the effective atomic number may be found in commonly owned U.S. Pat. Nos. 5,319,547; 5,600,700; 5,642, 393; 5,838,758; and 6,088,423, all of which are hereby incorporated by reference in their entirety.

Accordingly, a distribution of effective atomic number of the three-dimensional space may be determined.

A distribution of a density of the three-dimensional space is accessed (340). The distribution of the density may be a distribution of x-ray stopping power and the distribution may be obtained from a volumetric image of the three-dimensional space created by passing the broadband x-ray radiation through the three-dimensional space and generating a volumetric image based on sensed radiation. The x-ray stopping power represents the amount of penetration of an x-ray incident on a particular portion of the three-dimensional image. The volumetric image that is the distribution of the x-ray stopping power may be made up of voxels, each of which represents a volume within the three-dimensional space. The value of a particular voxel represents the x-ray stopping power of the portion of the three-dimensional space associated with that voxel. For example, if a voxel represents a bone region within a body of a patient, the value of the voxel is the x-ray stopping power of the bone region.

A conversion is applied to the distribution of the effective atomic number and the distribution of the density (350), and a distribution of the heavy particle stopping power is generated based on the conversion (360). The logarithm of the attenuation of an x-ray beam provides a quantity that is approximately proportionate to the line integral of the electron density along the path of the x-ray beam. However, the quantity is more accurately proportionate to the line integral of the x-ray stopping power. The x-ray stopping power is a combination of the input x-ray energy in KeV (E), electron density ($\rho$), and atomic number (Z) to the fourth power of the atoms in the material. The x-ray stopping power is shown below in Equation (1).

$$P_{stop}^{X\text{-}ray} \approx \rho \left[ \int d\ell \left( \begin{matrix} 10^{-33} \frac{Z^4}{E^{3.5}} + 5 \times 10^{-25} - \\ 10^{-25} \times \ln(E/100 \text{ keV}) \end{matrix} \right) \right] \quad \text{(Equation 1)}$$

Equation (1) may be rearranged as shown below in Equation (2) to more clearly show the contribution of the effective atomic number to the x-ray stopping power.

$$P_{stop}^{X\text{-}ray} \approx \rho \left[ \kappa(E) \int d\ell \left( 1 + \frac{Z^4}{E^{3.5}} \frac{10^{-8}}{1 - 0.2\ln(E/100 \text{ keV})} \right) \right], \quad \text{Equation (2)}$$

where $$\kappa(E) = 5 \times 10^{-25} [1 - 0.2\ln(E/100 \text{ keV})].$$

As shown by Equations (1) and (2), the x-ray stopping power and the density of the space are not directly proportional to each other, and the effective atomic number contributes to the difference between the two quantities. If there were only the "1" in the parenthetical portion of the x-ray stopping power represented in Equation (2), then the stopping power would be simply be proportional to density. However, the additional Z-dependent term in the parenthesis indicates that the x-ray stopping power does not reveal the density directly, and that a dual-energy decomposition of the X-ray stopping power that determines both ρ and $Z_{eff}$ yields more accurate results. Electron density is synonymous (up to a constant of proportionality) with mass density or simply density.

For heavy particle therapy, stopping power is a function of the hadron species (pion, proton, heavy ion), the hadron energy (e.g., the energy of the particle), the atomic number, and the electron density. For a given hadron therapy beamline (e.g., a beam of heavy particles produced by a heavy particle therapy system and directed toward a patient), the hadron energy and atomic number are known, and the effective atomic number and electron density are the quantities that are mapped or determined in the patient. The distribution of the effective atomic number and the density are determined as discussed above. The conversion applied to the distribution of effective atomic number and the distribution of the x-ray stopping power (referred to as above 360) to determine a distribution of heavy particle stopping power is represented as shown in Equation (3):

Heavy Particle Stopping Power$(x,y,z)=$
$f_{ZI,E}(Z_{eff}(x,y,z))*\rho(x,y,z)$ Equation (3).

In Equation (3), $f_{ZI,E}$ is a function family for the heavy particle $Z_I$ at energy E. The heavy particle $Z_I$ is the effective atomic number of the ion species of the heavy particle used in the heavy particle beam at the energy of the beam. The ion species and the energy of the beam are known based on the type of therapy to be applied. The functions are different for each value of $Z_{eff}$ encountered by the hadron (or other heavy particle). In Equation (3), (x,y,z) represents a volumetric point within the patient, and $Z_{eff}(x,y,z)$ is the volumetric distribution atomic number in the patient, obtained by analysis of dual-energy x-ray data (e.g., the Alvarez-Macovsky technique) as discussed above in (330). In Equation (3), ρ(x,y,z) is the electron density. The energy deposition along the hadron path is determined by summing the heavy particle stopping power (x,y,z) along the planned path of the hadron through the patient. The planned path of the hadron or other heavy particle is the path through the patient to the target space (e.g., the space where the tumor is located).

Thus, a conversion as shown in Equation (3) is applied to the distribution of the effective atomic number and the x-ray stopping power to determine a volumetric distribution of the heavy particle stopping power as a function of (x,y,z). In some implementations, a two-dimensional distribution of the heavy particle stopping power may be determined by taking a slice from the volumetric heavy particle stopping power.

The contribution of the effective atomic number may account for several percent of the stopping power. In some examples, ignoring the effect of the effective atomic number may result in a stopping power that is inaccurate by a centimeter. Using a stopping power that is off by about a centimeter may result in delivery of a heavy particle a centimeter away from a tumor to be treated. Because of the highly localized nature of the heavy particle treatment and the relatively small distances between objects in the patient's body, the centimeter discrepancy may result in damage to healthy tissue and no damage to the tumor.

Accordingly, by determining the effective atomic number distribution for the patient and accounting for the effective atomic number when determining the heavy particle stopping power, the heavy particle treatment accuracy may be improved.

The distribution of the heavy particle stopping power may be used to plan a treatment with heavy particles such as protons, heavy ions, or hadrons. The heavy particle stopping power for each of the listed heavy particles is proportional to the heavy power stopping power for the other heavy particles. The distribution of the heavy power stopping power for a particular particle (such as protons) may be converted to the distribution for another heavy particle (such as heavy ions) using known functions.

A number of implementations have been described. Nevertheless, it will be understood that various modifications may be made without departing from the scope of the disclosure.

What is claimed is:

1. A system for determining a distribution of heavy particle stopping power of a patient, the system comprising:
   a broadband source of dual-energy x-rays, the broadband source configured to:
      produce a beam of broadband x-ray radiation, the broadband beam including energy having a first energy spectrum and a first peak energy and energy having a second energy spectrum and a second peak energy, and
      irradiate a three-dimensional space within a patient with the beam of broadband x-ray radiation;
   a detector system comprising a sensor configured to:
      sense radiation from the three-dimensional space, the sensed radiation including radiation caused by irradiating the three-dimensional space with the broadband source, and
      produce a representation of the sensed radiation; and
   a processor operable to:
      receive the representation of the sensed radiation,
      determine a distribution of effective atomic number of the three-dimensional space based on the representation from the detector system,
      determine a distribution of an x-ray stopping power of the three-dimensional space based on the representation from the detector system, the x-ray stopping power of the three-dimensional space being an indication of a depth of penetration of an x-ray incident on the three-dimensional space,
      apply a conversion to the distribution of the x-ray stopping power and the distribution of the effective atomic number, and
      generate a distribution of a heavy particle stopping power of the three-dimensional space based on the conversion, the heavy particle stopping power being used to indicate a depth of penetration for a heavy particle incident on the three-dimensional space.

2. The system of claim 1, wherein the processor is further operable to produce an input sufficient to define a heavy particle treatment based on the heavy particle stopping power, the input including a depth of penetration for a particular heavy particle.

3. The system of claim 1, further comprising a heavy particle therapy system comprising:
   a source of heavy particles configured to:
      produce a beam including a heavy particle, and
      direct the beam to a position within the three-dimensional space; and
   an input module configured to receive the distribution of the heavy particle stopping power of the three-dimensional space from the processor.

4. The system of claim 3, wherein the heavy particle therapy system and the broadband source of dual-energy x-rays are co-located.

5. The system of claim 4, wherein the heavy particle therapy system and the broadband source of dual-energy x-rays are located on a gantry.

6. The system of claim 1, further comprising a gantry on which the broadband source of dual-energy x-rays and the detector system are mounted.

7. The system of claim 1, wherein the broadband source of dual-energy x-rays comprises a single broadband source that is switchable between a first mode and a second mode, the single broadband source producing a first x-ray beam in the first mode and a second x-ray beam in the second mode, the first x-ray beam having the first energy spectrum and the first peak energy, and the second x-ray beam having the second energy spectrum and the second peak energy.

8. The system of claim 1, wherein the broadband source of dual-energy x-rays comprises: a first broadband source configured to produce a first x-ray beam having the first energy spectrum and the first peak energy, and
a second broadband source separate from the first broadband source and configured to produce a second x-ray beam having the second energy spectrum and the second peak energy.

9. The system of claim 1, wherein the detector system further comprises a detector configured to detect photons.

10. The system of claim 1, wherein the detector system is positioned opposite the three-dimensional space relative to the broadband source.

11. A system for determining a distribution of heavy particle stopping power of a patient, the system comprising:
a broadband source of x-rays configured to:
produce a single beam of broadband x-ray radiation having an energy spectrum and a peak energy, and
irradiate a three-dimensional space within a patient with the beam of broadband x-ray radiation;
a dual-energy detector system comprising a first sensor including a first sensor relatively more sensitive to a first band of energies included in the broadband x-ray radiation, and a second sensor relatively more sensitive to a second band of energies included in the broadband x-ray radiation, the second band of energies being higher than the first band of energies, and the sensor being configured to:
sense radiation from the three-dimensional space, the sensed radiation including radiation caused by irradiating the three-dimensional space with the broadband source, and
produce a representation of the sensed radiation; and
a processor operable to:
receive the representation of the sensed radiation,
determine a distribution of effective atomic number of the three-dimensional space based on the representation from the detector system,
determine a distribution of an x-ray stopping power of the three-dimensional space based on the representation from the detector system, the x-ray stopping power of the three-dimensional space being an indication of a depth of penetration of an x-ray incident on the three-dimensional space,
apply a conversion to the distribution of the x-ray stopping power and the distribution of the effective atomic number, and
generate a distribution of a heavy particle stopping power of the three-dimensional space based on the conversion, the heavy particle stopping power being used to indicate a depth of penetration for a heavy particle incident on the three-dimensional space.

12. A non-transitory computer-readable storage medium storing instructions, that when executed, cause a processor to perform the following operations:
access data reflecting an interaction between a broadband x-ray beam and a three-dimensional space of a patient, the broadband x-ray beam including a first energy band having a first energy spectrum and a first peak energy, and a second energy band having a second energy spectrum and a second peak energy higher than the first peak energy;
analyze the accessed data to determine an interaction between the three-dimensional space and the first energy band and an interaction between the three-dimensional space and the second energy band;
determine a distribution of effective atomic number of a three-dimensional space based on the interactions between the three-dimensional space and the first and second energy bands;
access a distribution of x-ray stopping power of the three-dimensional space;
apply a conversion to the distribution of the effective atomic number and the distribution of the x-ray stopping power of the three-dimensional space; and
generate, based on the conversion, a heavy particle distribution that represents a heavy particle stopping power of the three-dimensional space, the heavy particle stopping power being used to indicate a depth of penetration for a heavy particle incident on the three-dimensional space.

13. The medium of claim 12, wherein the instructions further comprise instructions, that when executed, cause the processor to provide inputs sufficient to define a heavy particle treatment that is directed toward a particular space within the three-dimensional space, the inputs being derived from the heavy particle distribution and the inputs including a depth of penetration for a particular heavy particle.

14. The medium of claim 13, wherein the inputs include a three-dimensional location of a target space within a body of a patient.

15. The medium of claim 13, wherein the particular heavy particle is one of a proton, a heavy ion, or a pion.

16. The medium of claim 12, wherein the first energy spectrum and the second energy spectrum overlap.

17. The medium of claim 12, wherein the three-dimensional space is represented by one or more voxels, and the distribution of the effective atomic number includes an effective atomic number for each voxel.

18. The medium of claim 12, wherein the heavy particle distribution is a volumetric heavy particle stopping power distribution.

19. The medium of claim 12, wherein the heavy particle distribution is a two-dimensional stopping power distribution.

20. A non-transitory computer-readable storage medium storing instructions, that when executed, cause a processor to perform the following operations:
access a distribution of effective atomic number of a three-dimensional space;
access a distribution of an x-ray stopping power of the three-dimensional space;
apply a conversion to the distribution of the effective atomic number and the distribution of x-ray stopping power; and
generate a distribution of the heavy particle stopping power of the three-dimensional space based on the conversion, the heavy particle stopping power being an indication of a depth of penetration for a heavy particle incident on the three-dimensional space.

21. The medium of claim 20, wherein the distribution of the heavy particle stopping power distribution is a volumetric distribution.

22. The medium of claim 20, wherein the distribution of the heavy particle stopping power distribution is a two-dimensional distribution.

23. A method for determining a distribution of heavy particle stopping power, the method comprising:
   accessing a distribution of effective atomic number of a three-dimensional space;
   accessing a distribution of an x-ray stopping power of the three-dimensional space;
   applying a conversion to the distribution of the effective atomic number and the distribution of x-ray stopping power; and
   generating a distribution of the heavy particle stopping power of the three-dimensional space based on the conversion, the heavy particle stopping power being an indication of a depth of penetration for a heavy particle incident on the three-dimensional space.

24. The method of claim 23, further comprising, providing inputs sufficient to define a heavy particle treatment that is directed toward a particular space within the three-dimensional space, the inputs being derived from the distribution of heavy particle stopping power and the inputs including a depth of penetration for a particular heavy particle.

25. The method of claim 23, wherein the distribution of the heavy particle stopping power distribution is distribution of more than two dimensions.

26. The method of claim 22, wherein the distribution of the heavy particle stopping power distribution is a two-dimensional distribution.

27. The medium of claim 20, wherein the instructions further comprise instructions, that when executed, cause the processor to provide inputs sufficient to define a heavy particle treatment that is directed toward a particular space within the three-dimensional space, the inputs being derived from the distribution of heavy particle stopping power and the inputs including a depth of penetration for a particular heavy particle.

28. A system comprising:
   a source of broadband radiation configured to produce radiation and irradiate a three-dimensional space;
   a detector system comprising a sensor configured to:
      sense radiation from the three-dimensional space, the sensed radiation including radiation caused by irradiating the three-dimensional space with the source, and
      produce a representation of the sensed radiation; and
   a processor operable to:
      access a distribution of effective atomic number of a three-dimensional space;
      access a distribution of an x-ray stopping power of the three-dimensional space;
      apply a conversion to the distribution of the effective atomic number and the distribution of x-ray stopping power; and
      generate a distribution of the heavy particle stopping power of the three-dimensional space based on the conversion, the heavy particle stopping power being an indication of a depth of penetration for a heavy particle incident on the three-dimensional space.

* * * * *